US009943582B2

(12) United States Patent
Tinker

(10) Patent No.: US 9,943,582 B2
(45) Date of Patent: Apr. 17, 2018

(54) CHOLERA TOXIN CHIMERA AND ITS USE AS A STAPH VACCINE

(71) Applicant: BOISE STATE UNIVERSITY, Boise, ID (US)

(72) Inventor: Juliette Tinker, Eagle, ID (US)

(73) Assignee: Boise State University, Boise, ID (US)

(*) Notice: Subject to any disclaimer, the term of this patent is extended or adjusted under 35 U.S.C. 154(b) by 0 days.

(21) Appl. No.: 14/456,090

(22) Filed: Aug. 11, 2014

(65) Prior Publication Data

US 2015/0017199 A1 Jan. 15, 2015

Related U.S. Application Data

(63) Continuation of application No. 13/896,854, filed on May 17, 2013, now Pat. No. 8,911,748, which is a continuation of application No. 13/328,686, filed on Dec. 16, 2011, now Pat. No. 8,834,898.

(51) Int. Cl.

| | |
|---|---|
| *A61K 39/085* | (2006.01) |
| *A61K 39/02* | (2006.01) |
| *C07K 14/28* | (2006.01) |
| *C07K 14/315* | (2006.01) |
| *C07K 14/31* | (2006.01) |
| *A61K 39/00* | (2006.01) |

(52) U.S. Cl.

CPC .......... *A61K 39/085* (2013.01); *A61K 39/107* (2013.01); *C07K 14/28* (2013.01); *C07K 14/31* (2013.01); *C07K 14/315* (2013.01); *A61K 2039/55516* (2013.01); *A61K 2039/575* (2013.01); *A61K 2039/6037* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 6,030,624 | A | 2/2000 | Russell et al. | |
| 7,091,332 | B1 | 8/2006 | Bramley et al. | |
| 2007/0134263 | A1* | 6/2007 | Anderson et al. | 424/190.1 |
| 2013/0266607 | A1 | 10/2013 | Tinker | |

OTHER PUBLICATIONS

Tinker and Arlian. In: Program with Abstracts of Proceedings of the American Association for the Advancement of Science, Pacific Division, Southern Oregon University, Ashland, OR, Jun. 13-17, 2010, vol. 29, part I, #16, p. 68, Jun. 13, 2010.*

Arlian et al., Clin. Vaccine Immunol. 18: 1543-1551, epub Jul. 6, 2011.

Clarke et al., "Iron-regulated surface determinant protein A mediates adhesion of *Staphylococcus aureus* to human corneocyte envelope proteins", Infection and Immunity, 77(6), 2408-2416 Dec. 31, 2009.

Clarke et al., "IsdA protects *Staphylococcus aureus* against the bactericidal protease activity of apolactoferrin", Infection and Immunity, 76(4), 1518-1526 Dec. 31, 2008.

F. Van Den Akker et al., "Crystal Structure of a New Heat-Labile Enterotoxin, LT-IIB", 4(6), 665-678 Dec. 31, 1996.

F. Van Den Akker et al., "Crystal Structure of Heat-Labile Enterotoxin from *Escherichia coli* with Increased Thermostability Introduced by an Engineered Disulfide Bond in the A Subunit", Protein Science, 6, 2644-2649 Dec. 31, 1997.

Fraser et al., "Structure of Shiga Toxin Type 2 (Stx2) from *Escherichia coli* O157:H7", 279(26), 27511-27517 Dec. 31, 2004.

Greenspan et al., Nature Biotechnology 7, 936-937 Dec. 31, 1999.

Grigg et al., "Heme coordination by *Staphylococcus aureus* IsdE", Journal of Biological Chemistry, 282, 28815-28822 Dec. 31, 2007.

Houghten et al., "New Approaches to Immunization", Vaccines 86, Cold Spring Harbor Laboratory, 21-25 Dec. 31, 1986.

Klevens et al., "Invasive methicillin-resistant *Staphylococcus aureus* infections in the United States", The Journal of the American Medical Association, 298(15), 1763-1771 Dec. 31, 2007.

Kuehnert et al., "Prevalence of *Staphylococcus Aureus* Nasal Colonization in the United States", National Center for Infectious Diseases, JID 2006, 172-179 Dec. 31, 2005.

Lowy, Fd., "*Staphylococcus aureus* infections", New England Journal of Medicine, 339, 520-532 Dec. 31, 1998.

Sixma et al., "Refined Structure of *Escherichia coli* Heat-Labile Enterotoxin, A Close Relative of Cholera Toxin", J. Med. Biology, 230, 890-918 Dec. 31, 1993.

Skolnick et al., Trends in Biotechnology 18, 34-39 Dec. 31, 2000.

Stranger-Jones et al., "Vaccine assembly from surface proteins of *Staphylococcus aureus*", PNAS 103, 16942-16947 Dec. 31, 2006.

Tinker, J., "Characterization of the immune response to *Staphylococcal* enterotoxin chimeras in mice", DIALOG file 266, FEDRIP Sep. 9, 2010.

Von Eiff et al., Diagn. Microbiol. Infect. Dis. 58, 297-302 Dec. 31, 2007.

Zhang et al., "The Three-Dimensional Crystal Structure of Cholera Toxin", J. Mol. Biology, 251, 563-573 Dec. 31, 1995.

* cited by examiner

*Primary Examiner* — S. Devi

(74) *Attorney, Agent, or Firm* — McKee, Voorhees & Sease, PLC

(57) ABSTRACT

The present invention relates to chimeric protein vaccines and methods of use thereof in the treatment of *Staphylococcus aureus*. One embodiment of the present invention provides a method of generating an immune response in a mammal, that includes administering to the mammal, a composition having a chimeric protein having at least one of: a portion of a cholera toxin, a portion of a heat-labile toxin, and a portion of a shiga toxin; and an antigen having at least one of: an antigenic material from *S. aureus* and an antigenic material from a *S. aureus*-specific polypeptide.

12 Claims, 9 Drawing Sheets

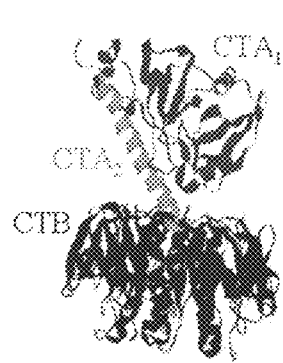 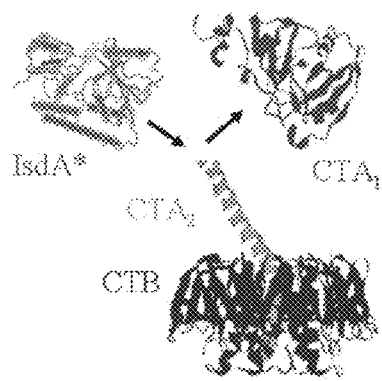 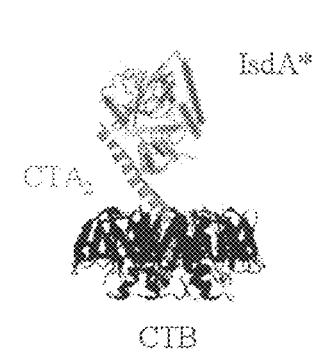
FIG. 1A  FIG. 1B  FIG. 1C
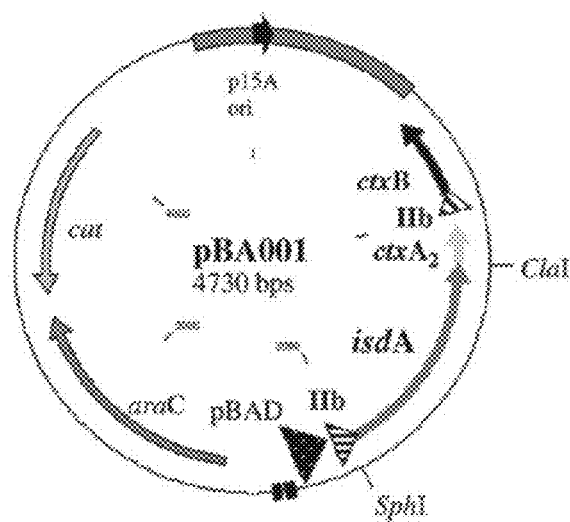
FIG. 2

FIG. 5A    FIG. 5C
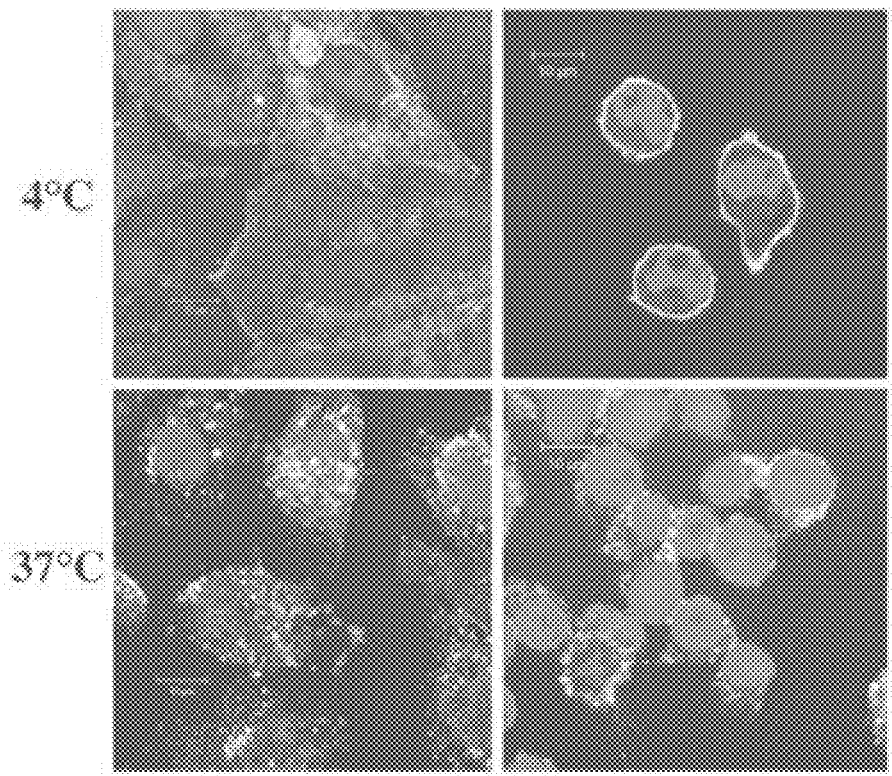
FIG. 5B    FIG. 5D
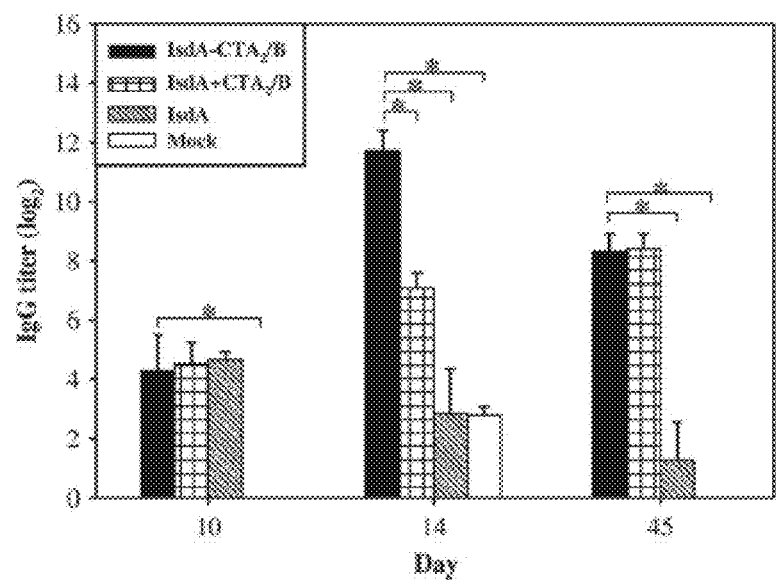
FIG. 6

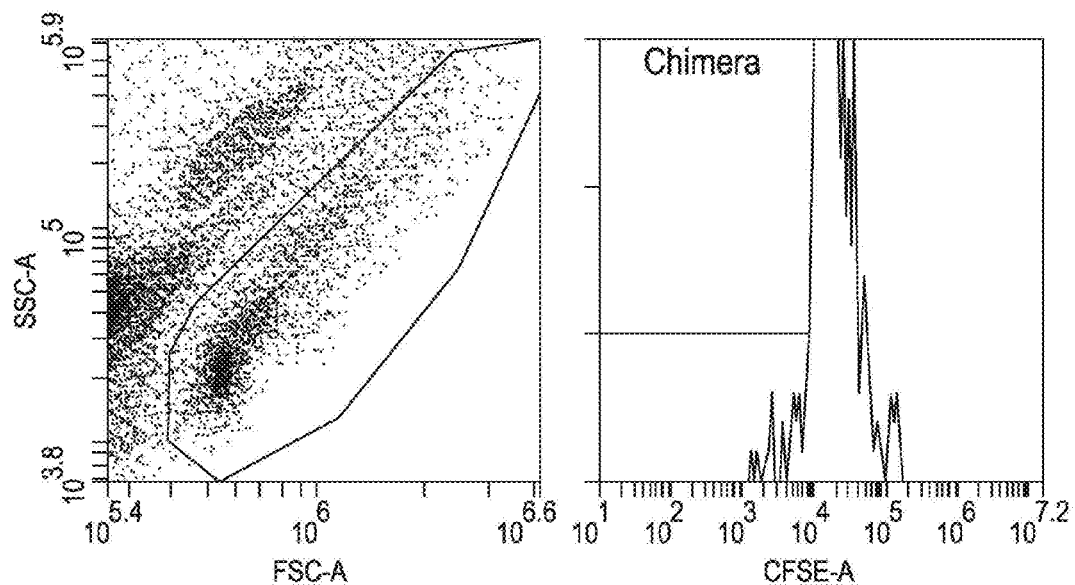
FIG. 8A
FIG. 8C
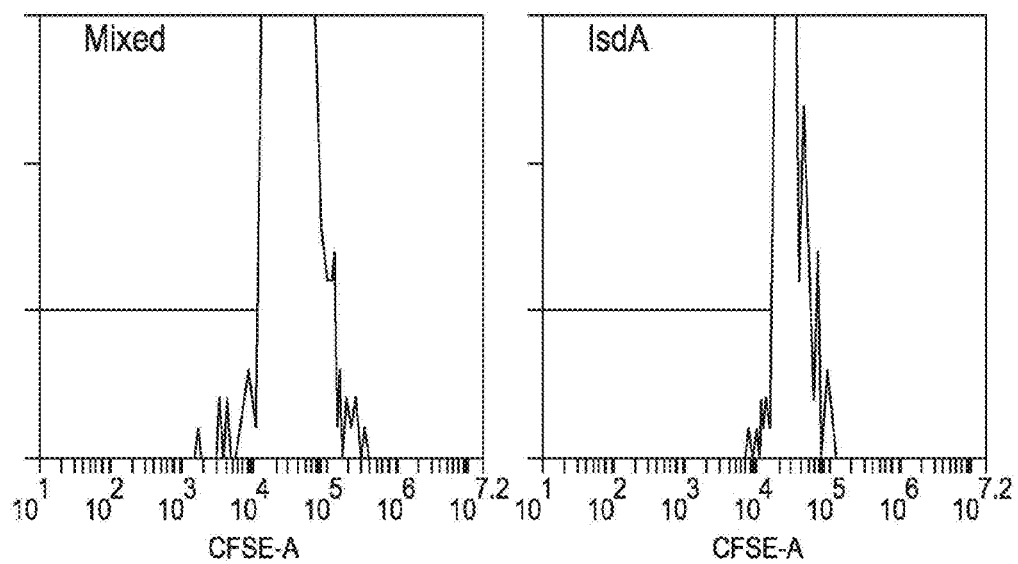
FIG. 8B
FIG. 8D

CHOLERA TOXIN CHIMERA AND ITS USE AS A STAPH VACCINE

CROSS-REFERENCE TO RELATED APPLICATIONS

This application is a continuation of U.S. patent application Ser. No. 13/896,854, filed May 17, 2013, now U.S. Pat. No. 8,911,748 issued Dec. 16, 2014. This application is also a continuation of U.S. patent application Ser. No. 13/328,686 filed Dec. 16, 2011, now U.S. Pat. No. 8,834,898 issued Sept. 16, 2014.

GRANT REFERENCE

This invention was made with government support under grant numbers 2009- 65119-05977 and 2015-67016-22976 awarded by the U.S. Department of Agriculture/National Institute of Food and Agriculture, grant number RR025014 awarded by the National Institutes of Health, and grant number W81XWH-09-1-0588 awarded by the Army Medical Research and Materiel Command. The government has certain rights in the invention.

SEQUENCE LISTING

The instant application contains a Sequence Listing which was the only Sequence Listing filed in the parent case U.S. application Ser. No. 13/328,686 (now U.S. Pat. No. 8,834,898), filed Jun. 20, 2013. The Sequence Listing was compliant with 37 CFR 1.821-1.825, and is used as the computer readable form for the present application, in accordance with 37 CFR 1.821(e).

BACKGROUND

The present invention relates to infectious diseases and, more particularly, to chimeric protein vaccines and methods of use thereof in the treatment of *Staphylococcus aureus.*

*Staphylococcus aureus* (*S. aureus*) is a common cause of hospital-acquired infections and represents an important public health threat. *S. aureus* can cause nosocomial (hospital) and community-acquired infections including impetigo, cellulitis, food poisoning, toxic shock syndrome, invasive necrotizing pneumonia, and endocarditis. *S. aureus* is also the most common species of staphylococci to cause Staph infections. Currently, it is one of the top causes of infectious disease deaths in the United States.

*S. aureus* also causes mastitis, which is a major problem in dairy cows with considerable economic implications. For example, mastitis in dairy cows is most commonly caused by *S. aureus* and is one of the most common diseases infecting dairy cattle in the United States. *S. aureus* causes a persistent, inflammatory reaction of the udder tissue that can lead to chronic infections that result in the cow being culled from the herd. Milk from cows with mastitis also typically have higher somatic cell count, which generally lowers the milk quality. It is estimated that mastitis may cost the dairy industry billions of dollars per year in economic losses.

A growing concern in the treatment of *S. aureus* is that the bacterium is often resistant to multiple antibiotics. Roughly half of the nosocomial isolates in the United States are methicillin-resistant *S. aureus* (MRSA). Methicillin-resistant *S. aureus* is also sometimes referred to as "multidrug-resistant" *S. aureus* or "oxacillin-resistant *S. aureus*." MRSA bacterium is generally resistant to beta-lactam antibiotics, which include the penicillins (e.g., methicillin, dicloxacillin, nafcillin, oxacillin, etc.) and cephalosporins. Currently, a vaccine that prevents staphylococcal disease is unavailable.

A possible approach for staphylococcal vaccine development is to target virulence factors such as toxins, enzymes, polysaccharide capsules, adhesive factors, and the like. A key to the possible vaccine approach may be that the anterior nares of humans are known to be an important niche for *S. aureus*. It is believed that nasal carriage is a major risk factor for invasive infection.

One potential *S. aureus* virulence factor is the iron-regulated surface determinant A (IsdA). IsdA is an *S. aureus* surface adhesin protein that may be immunogenic in certain organisms. IsdA can bind to human desquamated nasal epithelial cells and is believed to play a critical role in nasal colonization.

However, a major obstacle in vaccine development of *S. aureus* is the lack of immunostimulatory adjuvants that can function from mucosal surfaces. While certain toxins (e.g., cholera toxin and heat-labile toxin) have the ability to induce mucosal and systemic immune responses to co-administered antigens, these bacterial proteins are generally too toxic for human use.

SUMMARY OF THE INVENTION

The present invention relates to infectious diseases and, more particularly, to chimeric protein vaccines and methods of use thereof in the treatment of *Staphylococcus aureus.*

In some embodiments, the present invention provides methods of generating an immune response in a mammal comprising: administering to the mammal a composition comprising: a chimeric protein comprising at least one of: a portion of a cholera toxin, a portion of a heat-labile toxin, and a portion of a shiga toxin; and an antigen comprising at least one of: an antigenic material from *S. aureus* and an antigenic material from an *S. aureus*-specific polypeptide.

In other embodiments, the present invention provides methods of vaccinating a cow comprising: administering to the cow a chimeric protein comprising: an adjuvant selected from the group consisting of: a portion of a cholera toxin, a portion of a heat-labile toxin, a portion of a shiga toxin, and any combination thereof; and an antigen selected from the group consisting of: an antigenic material from *S. aureus*, an antigenic material from a *S. aureus*-specific polypeptide, and any combination thereof.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to those skilled in the art and having the benefit of this disclosure.

FIGS. 1A-1C show ribbon diagrams illustrating structures of cholera toxin, IsdA, and chimeric protein according to some embodiments.

FIG. 2 shows a diagram illustrating a plasmid that encodes a chimeric protein according to some embodiments.

FIGS. 3A-3B illustrate expression and purification of a chimeric protein according to some embodiments.

FIGS. 5A-5D show confocal images of chimeric protein binding to Vero and DC2.4 cells stained with fluorescent dyes according to some embodiments.

FIG. 6 shows a plot showing in vivo systemic antibody response to chimeric protein according to some embodiments.

FIGS. 8A-8D show plots showing the results of flow cytometry experiments on the proliferation of T lymphocytes from mice immunized with chimeric protein according to some embodiments.

DETAILED DESCRIPTION

Figures 3A, 3B:
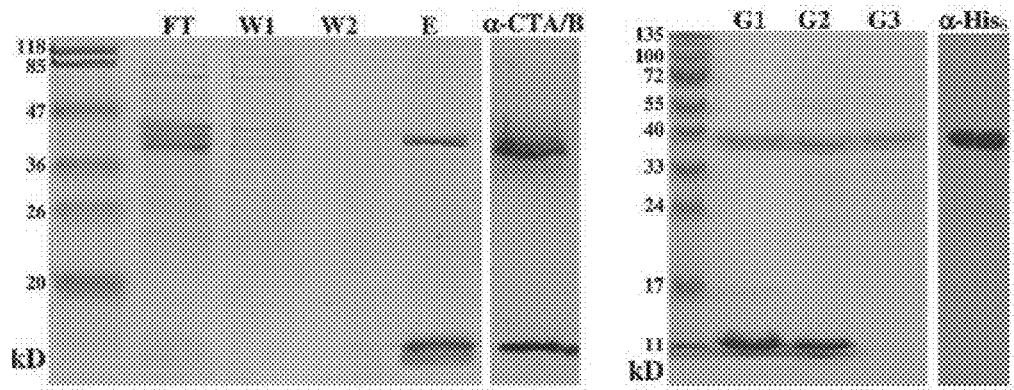

The present invention relates to infectious diseases and, more particularly, to chimeric protein vaccines and methods of use thereof in the treatment of *Staphylococcus aureus*.

There are a number of advantages related to the present invention. The present invention provides compositions (in some embodiments, chimeric proteins) that may be useful as vaccines against various strains of *S. aureus* and related bacteria in various organisms (e.g., mammals such as humans, cows, etc.).

As used herein, the term "chimeric protein" generally refers to any protein comprised of a first amino acid sequence derived from a first source, bonded, covalently or non-covalently (e.g., hydrogen bonding, van der Waals force, hydrophobic interaction, etc.), to a second amino acid sequence derived from a second source, wherein the first and second source are not the same. A first source and a second source that are not the same can include two different biological entities, or two different proteins from the same biological entity, or a biological entity and a non-biological entity. A chimeric protein can include for example, a protein derived from at least 2 different biological sources. A biological source can include any non-synthetically produced nucleic acid or amino acid sequence (e.g., a genomic or cDNA sequence, a plasmid or viral vector, a native virion or a mutant or analog, as further described herein, of any of the above). A synthetic source can include a protein or nucleic acid sequence produced chemically and not by a biological system (e.g., solid phase synthesis of amino acid sequences). A chimeric protein can also include a protein derived from at least 2 different synthetic sources or a protein derived from at least one biological source and at least one synthetic source. For the purposes of this disclosure, a chimeric protein may or may not be a single polypeptide (i.e., a fusion protein).

In some embodiments, the vaccines may be prophylactic and may be administered before the onset of *S. aureus* related infections. It is believed that the vaccines of the present invention can activate humoral responses, stimulate protection, and block the promotion of oral tolerance against *S. aureus*. Currently, there are no known vaccines that can prevent Staphylococcal infection.

The present invention provides compositions that comprise a first amino acid sequence derived from a suitable adjuvant source and a second amino acid sequence derived from a suitable antigen source. In some embodiments, the composition may have multiple functions. For example, the first amino acid sequence may act as an adjuvant while the second amino acid sequence may act as an antigen. As used herein, the term "amino acid sequence" does not necessarily imply a single polypeptide. In other words, the amino acid sequence derived from a suitable adjuvant source may not necessarily be confined to a single polypeptide. For example, a portion of the amino acid sequence may be in one polypeptide while the remaining portion of the amino acid sequence may reside in another polypeptide.

In some embodiments, the composition may be a single polypeptide (e.g., a fusion protein). In other embodiments, the composition may be assembled from two or more polypeptides. In certain embodiments having two or more polypeptides, one or more polypeptide may be chimeric. In certain embodiments, the two or more polypeptides may fold or assemble together within a suitable expression system (e.g., *E. coli*) or by any other suitable method (e.g., by the use of chaperone molecules).

The adjuvants typically used to construct the chimeric proteins of the present invention may be non-toxigenic or less toxigenic than full-length or non-chimeric toxins and yet retain their potent adjuvant characteristics. In some embodiments, the adjuvant may have been modified from a toxigenic adjuvant source with a modification that renders the adjuvant non-toxigenic or less toxigenic and likely suitable for mucosal surfaces. Such modifications may include, but are not limited to, mutation of amino acid, removal of toxigenic subunits, and the like.

As used herein, an "adjuvant" generally refers to a pharmacological or an immunological agent that modifies the effect of other agents (e.g., drug or vaccine), while having few if any direct effects when given by itself. An immunological adjuvant is often included in vaccines to enhances the recipient's immune response to the antigen, while keeping the injection of foreign material to a minimum. For the purposes of this disclosure, an adjuvant may be linked covalently or non-covalently to the antigen.

While cholera toxin is an example of a potent adjuvant, it remains mostly unsuitable for use in humans. Specifically, there are safety concerns with the mucosal administration of cholera toxin and other similar toxins such as heat-labile toxin and shiga toxin. It is believed that such administration can redirect antigens to the central nervous system through GM1-dependent binding to olfactory epithelium. It has been previously difficult to separate the toxigenicity and adjuvanticity of cholera toxin, heat-labile toxin, and/or shiga toxin.

In some embodiments, the adjuvant source may be a toxin. The adjuvant may be coupled, assembled, folded, fused, or otherwise associated with an antigen to form a composition that further enhances the immunogenic effects of the antigen. Examples of suitable toxins include, but are not limited to, cholera toxin (CT), shiga toxin (ST1, ST2, etc.), heat-labile toxin (LT, LT-IIa, LT-IIb, etc.) from *E. coli*.

In some preferred embodiments, the toxins are modified to be non-toxigenic while remaining potent immunostimulatory molecules that can bind to and target immune effector cells at mucosal site. It is believed that both shiga toxin and heat-labile toxin are structurally similar or analogous to cholera toxin.

In particular, cholera toxin is a protein secreted by the bacterium *Vibrio cholerae* and is generally responsible for the massive, watery diarrhea characteristic of cholera infection. Structurally, cholera toxin is an oligomeric complex made up of six protein subunits: a single copy of the A subunit (part A, enzymatic), and five copies of the B subunit (part B, receptor binding). The A subunit has two important segments: the A1 domain ($CTA_1$), which is toxigenic and the A2 domain ($CTA_2$), which forms an extended alpha helix that sits snugly in the central pore of the B subunit ring.

FIG. 1A shows a ribbon diagram of the cholera toxin crystal structure showing the $CTA_1$ domain (SEQ ID NO: 1) and connecting $CTA_2$ domain (SEQ ID NO:2), and the B subunit (SEQ ID NO: 3).

It is believed that cholera toxin immunomodulation may be involved in the activation of antigen-presenting cells, promotion of B-cell isotype switching, and upregulation of costimulatory and major histocompability complex (MHC) class II expression. Many of these responses result from the interaction of the cholera toxin B (CTB) subunit with the ganglioside GM1 receptor on effector cells, such as dendritic cells, that promote antigen uptake, presentation, and cellular activation. Thus, suitably modified non-toxigenic forms of cholera toxin by itself may act as an antigen carrier and be highly immunostimulatory. Without being limited by theory, it is believed that heat-labile toxin and shiga toxin are structurally and functionally similar (e.g., adjuvanticity) to the cholera toxin. For example, heat-labile toxin has an $A_1$ domain (SEQ ID NO: 7), $A_2$ domain (SEQ ID NO: 8), B domain (SEQ ID NO: 9) analogous to the $A_1$, $A_2$, and B domains of cholera toxin. An IsdA-$LTA_2$/B chimeric protein may have a sequence shown in SEQ ID NO: 10.

An antigen is generally any substance that causes the production of antibodies against it. An antigen may be a foreign substance from the environment or it may also be formed within the environment, such as bacterial toxins or tissue cells. Examples of a suitable antigen source include, but are not limited to, iron-regulated surface determinant A, iron-regulated surface determinant B (IsdB), clumping factor A (ClfA), clumping factor B (ClfB), fibronectin-binding protein (FnBP), penicillin binding protein 2a (PBP2A), serine-aspartate rich fibrinogen sialoprotein binding protein (SrdE), and the like.

In particular, the N-terminal near iron transporter (NEAT) domain of IsdA is capable of binding to a broad spectrum of human ligands, including transferring heme, fibrinogen, fibronectin, and corneocyte envelope proteins to mediate adherence and dissemination of *S. aureus*. The C-terminal domain of IsdA defends *S. aureus* against human skin bactericidal fatty acids and antimicrobial peptides by making the cell surface hydrophilic.

FIG. 1B shows a ribbon diagram of IsdA antigen (SEQ ID NO: 4) that is replacing the toxigenic $CTA_1$ domain (SEQ ID NO: 1) to construct a chimeric protein that comprises an antigen and a non-toxigenic adjuvant. FIG. 1C shows a ribbon diagram of one preferred chimeric protein, IsdA-$CTA_2$/B (SEQ ID NO: 5).

Some embodiments provide compositions comprising: a chimeric protein comprising at least one of: a portion of a cholera toxin, a portion of a heat-labile toxin, and a portion of a shiga toxin; and an antigen comprising at least one of: an antigenic material from *S. aureus* and an antigenic material from a *S. aureus*-specific polypeptide.

In some embodiments, the composition is a fusion protein. In certain embodiments, the composition is a single polypeptide.

Some embodiments provide a chimeric protein comprising: an adjuvant and an antigen. The adjuvant may be selected from the group consisting of: a portion of a cholera toxin, a portion of a heat-labile toxin, a portion of a shiga toxin, and combinations thereof. The antigen may be selected from the group consisting of: an antigenic material from *S. aureus* (e.g., carbohydrates, peptides, etc.), an antigenic material from an *S. aureus*-specific polypeptide, and combinations thereof.

In some embodiments, the adjuvant is one of: $CTA_2$/B, $LTA_2$/B, or $STA_2$/B. In one or more embodiments, the adjuvant further includes at least one additional cholera toxin B subunit, heat-labile toxin B subunit, or shiga toxin B subunit. In one or more embodiments, the adjuvant further comprises at least one additional cholera toxin $A_2$ subunit, heat-labile toxin $A_2$ subunit, or shiga toxin $A_2$ subunit.

While some preferred embodiments of the domain and chimeric protein sequences have been provided, the present invention may be practiced using any number of alternative embodiments. For example, it is well known in the relevant arts that protein or polypeptide variants typically retain their function as long as they are have sufficient sequence identity with their native sequences.

In some embodiments, the composition has at least about 80% sequence identity to SEQ ID NO: 5, 10, or 15. In some preferred embodiments, the composition has at least about 90% sequence identity to SEQ ID NO: 5, 10, or 15. In certain embodiments, the antigen portion of the composition has at least about 80% sequence identity to SEQ ID NO: 4. In some preferred embodiments, the antigen portion of the composition has at least about 90% sequence identity to SEQ ID NO: 4. In some embodiments, the composition is assembled from a first polypeptide and a second polypeptide that are non-covalently linked. In one or more of these embodiments, the first polypeptide has at least about 80% sequence identity to SEQ ID NO: 6, 11, or 16. In some preferred embodiments, the first polypeptide has at least about 90% sequence identity to SEQ ID NO: 6, 11, or 16. In some embodiments, the second polypeptide has at least about 80% sequence identity to SEQ ID NO: 3, 9, or 14. In some preferred embodiments, the second polypeptide has at least about 80% sequence identity to SEQ ID NO: 3, 9, or 14.

Generally, a chimeric protein will be comprised of a single $A_2$ subunit and a B subunit (from cholera toxin, heat-labile toxin, or shiga toxin). In some optional embodiments, the chimeric protein may further comprise at least one additional B subunit. In some optional embodiments, the chimeric protein may further comprise at least one additional $A_2$ subunit. In some embodiments, the subunits may be linked by a disulfide bond. In some embodiments, the disulfide bond may be engineered. In some embodiments, the antigen has a disulfide bond with the adjuvant. In some embodiments, the antigen is associated non-covalently with the adjuvant.

In some embodiments, the antigen comprises a sequence that has at least about 80% sequence identity to iron-regulated surface determinant A, iron-regulated surface determinant B (IsdB), clumping factor A (ClfA), clumping factor B (ClfB), fibronectin-binding protein (FnBP), fibronectin-binding protein (FnBP), penicillin binding protein 2a (PBP2A), or serine-aspartate rich fibrinogen sialoprotein binding protein (SrdE). In some preferred embodiments, the sequence identity is at least about 90%.

In some exemplary embodiments, the chimeric protein is IsdA-CTA$_2$/B (SEQ ID NO: 5). As used herein, "IsdA-CTA$_2$/B" generally refers to a chimeric protein that comprises an IsdA antigen domain, a CTA$_2$ subunit, and a CTB subunit. In some embodiments, each of the IsdA antigen domain (SEQ ID NO: 4), the CTA$_2$ domain (SEQ ID NO: 2) and the CTB domain (SEQ ID NO: 3) may be bonded covalently (e.g., peptide bonds, disulfide bonds, etc.) or non-covalently to at least one other domain. In some embodiments, the bond may be an engineered disulfide bond.

In some embodiments, the chimeric protein is IsdA-LTA$_2$/B (SEQ ID NO: 10). As used herein, "IsdA-LTA$_2$/B" generally refers to a chimeric protein that comprises an IsdA antigen domain, a LTA$_2$ subunit, and a LTB subunit. In some embodiments, each of the IsdA antigen domain (SEQ ID NO: 4), the LTA$_2$ subunit (SEQ ID NO: 8) and the CTB subunit (SEQ ID NO: 9) may be bonded covalently (e.g., peptide bonds, disulfide bonds, etc.) or non-covalently to at least one other domain. In some embodiments, the bond may be an engineered disulfide bond.

In some embodiments, the chimeric protein is IsdA-STA$_2$/B (SEQ ID NO: 15). As used herein, "IsdA-STA$_2$/B" generally refers to a chimeric protein that comprises an IsdA antigen domain, a STA$_2$ subunit, and a STB subunit. In some embodiments, each of the IsdA antigen domain (SEQ ID NO: 4), the STA$_2$ subunit (SEQ ID NO: 13) and the STB subunit (SEQ ID NO: 14) may be bonded covalently (e.g., peptide bonds, disulfide bonds, etc.) or non-covalently to at least one other domain. In some embodiments, the bond may be an engineered disulfide bond.

In some embodiments, the chimeric protein may further comprise modifications that enhance at least one of: solubility of the chimeric protein, specificity for *S. aureus*, specificity for GM1, expression of the chimeric protein, and immunogenicity of the chimeric protein.

Some embodiments provide methods for generating an immune response in a mammal comprising: administering to the mammal a composition (e.g., chimeric protein) according to one or more embodiments described herein.

In some embodiments, the mammal is selected from the group consisting of: a human, a cow, a dog, a cat, and a horse.

In some embodiments, the administration of the composition is by intranasal administration, oral administration, intramuscular administration, peritoneal administration, sublingual administration, transcutaneous administration, subcutaneous administration, intravaginal administration, or intrarectal administration. The administered dosage of the composition may generally be an amount suitable to elicit the desired immune response. In some embodiments, the administering to the mammal comprises: administering the composition to at least one cell from the mammal in vitro or in vivo.

Some embodiments provide methods for vaccinating a cow comprising: administering to the cow, a chimeric protein according to one or more embodiments described herein.

To facilitate a better understanding of the present invention, the following examples of preferred embodiments are given. In no way should the following examples be read to limit, or to define, the scope of the invention.

EXAMPLE 1

To direct the IsdA-CTA$_2$ and CTB peptides of the chimera to the *E. coli* periplasm for proper assembly, pBA001 (FIG. 2) was constructed from pARLDR19, which utilizes the *E. coli* LTIIb N-terminal leader sequence. Induction of pBA001 and purification from the periplasm of *E. coli* resulted in efficient IsdA-CTA$_2$/B production (3 to 4 mg from 1 liter of starting culture). SDS-PAGE analysis of the purification of IsdA-CTA$_2$/B and immunoblotting using antibodies against CTA and CTB (FIG. 3A) confirm that IsdA-CTA$_2$ (~38 kDa) was copurified with CTB (~11 kDa) on D-galactose agarose, which is indicative of proper chimera folding. Referring to FIG. 3A, the SDS-PAGE analysis shows flowthrough (FT), washes (W1 and W2) and elution (E) of IsdA-CTA$_2$/B from D-galactose affinity purification and anti-CTA/B Western blot of purified IsdA-CTA$_2$/B (~38 and 11 kDA).

IsdA alone was also purified using a six-histidine tag. FIG. 3B shows an SDS-polyacrylamide gel of all resulting proteins used in animal studies, as well as immunoblotting of purified IsdA with anti-His6 (~37 kDa): ISdA-CTA$_2$/B (G1), IsdA plus CTA$_2$/B mixed (G2), and IsdA (G3).

The following protocol was followed in order to obtain the chimeric proteins.

MRSA252 strain was used for IsdA isolation. MRSA USA300 (pvl mutant) strain was used in adhesion assays. *E. coli* TE1, a □endA derivative of TX1, and BL21(DE3)/pLysS strains were used for protein expression. All bacterial strains were cultured using Luria-Bertani (LB) agar or broth at 37° C. with chloramphenicol (35 □g/ml), ampicillin (100 □g/m), and/or kanamycin (50 □g/m).

To construct pBA001 plasmid (FIG. 2) for the expression of IsdA-CTA$_2$/B, IsdA was PCR amplified from MRSA252 with primers that add 5' SphI GCTACTGGCATGCG-GCAACAGAAGCTACGAAC (SEQ ID NO: 17) and 3' ClaI GTGCATGATCGATTTTGGTAATTCTTTAGC (SEQ ID NO: 18) sites (in boldface) and cloned into pARLDR19 between the LTIIb leader sequence and CTXA$_2$. CTB was also expressed from this vector. To make His6-IsdA, IsdA was amplified from MRSA252 with primers that add 5' BamHI GCTACTGGATCCGCGGCAACAGAAGCTAC-GAAC (SEQ ID NO: 19) or GTG-CATAAGCTTTCAAGTTTTTGGTAATTCTTTAGC (SEQ ID NO: 20) and 3' HindIII GTGCATGATCGATTTTGG-TAATTCTTTAGC (SEQ ID NO: 21) sites (in boldface) and cloned into pTrcHisA (Invitrogen, Carlsbad, Calif.) or pET-40b+, yielding pBA009A and pBA015. pARLDR19 was used to express CTA$_2$/B for the mixed preparation. Plasmids were transformed into *E. coli* TE1 (pBA001, pBA009A, and pARLDR19) or BL21(DE3)/pLysS (pBA015) and sequenced.

To express IsdA-CTA$_2$/B and CTA$_2$/B, cultures with pBA001 or pARLDR19 were grown to an optical density at 600 nm (OD600) of 0.9 and induced for 15 h with 0.2% L-arabinose. Proteins were purified from the periplasmic extract using immobilized D-galactose. For mock cultures, *E. coli* TE1 without plasmid was induced, and the periplasmic extract was purified. IsdA was isolated from the cytosol of cultures containing pBA009A and purified by cobalt affinity chromatography under denaturing conditions. IsdA was also purified from periplasmic extracts of cultures containing pBA015 over Talon resin under native conditions. All proteins were dialyzed against phosphate-buffered saline (PBS), reduced to <0.125 endotoxin units (EU)/ml lipopolysaccharide by passage through an endotoxin removal column, and quantified by bicinchoninic acid assay prior to the addition of 5% glycerol.

Proteins resolved by SDS-12% PAGE were stained with Coomassie® or transferred to nitrocellulose membranes. Membranes were blocked overnight with 5% skim milk in PBS plus 0.05% Tween® 20 (PBS-T), incubated with polyclonal anti-CTA (1:2,500) and anti-CTB (1:5,000) or anti-His6 (1:2,500), followed by horseradish peroxidase (HRP)-conjugated anti-rabbit IgG (1:5,000) and developed with IMMOBILON WESTERN HRP SUBSTRATE commercially available from Millipore, Billerica, Mass.

EXAMPLE 2

To compare the receptor binding affinity of purified IsdA-CTA$_2$/B chimera with native CT, ganglioside GM1 ELISA assays using anti-CTA and anti-CTB antibodies were performed.

GM1 enzyme-linked immunosorbent assays (ELISA) were performed by coating microtiter plates with 0.15 □M GM1 for 15 h at 20° C., blocking with 10% bovine serum albumin, and incubating with IsdA-CTA$_2$/B or CT for 1 h at 37° C. Ganglioside GM1 is found ubiquitously on mammalian cells and acts as the site of binding for both cholera toxin and heat-labile toxin. Plates were washed with PBS-T and incubated with anti-CTA (1:2,000) or anti-CTB (1:5,000) followed by HRP-conjugated anti-rabbit IgG, both for 1 h at 37° C. The reaction was developed with o-phenylenediamine dihydrochloride ($A_{450}$).

Figure 4:
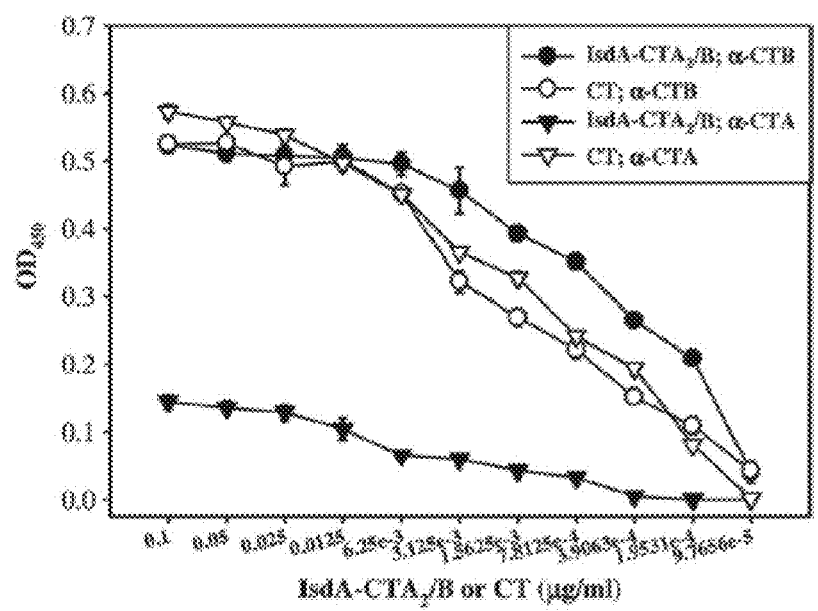
FIG. 4 shows a plot showing the results of a receptor binding affinity assay according to some embodiments.

The ELISA results indicate that the B subunit of IsdA-CTA$_2$/B has GM1 binding affinity similar to that of CT (FIG. 4). Low anti-CTA response from IsdA-CTA$_2$/B was an expected result from this fusion that contains only 46 bp of full-length CTA.

Confocal microscopy was used to further confirm receptor binding and internalization of IsdA-CTA$_2$/B into epithelial and dendritic cells (DC) in vitro. Immune effector cells, such as dendritic cells, have a uniquely high affinity for CT and non-toxigenic CTB. FIGS. 5A-5D show anti-CT FITC-labeled IsdA-CTA$_2$/B bound to the surface of cells (Vero epithelial cells in FIG. 5A-5B; DC cells in FIG. 5C-5D) at 4° C. and internalization after 45 min at 37° C., indicating that, at a minimum, the CTB subunit of the chimera were efficiently imported into the cell. These images obtained using polyclonal anti-CT and anti-rabbit-FITC with DAPI suggest that IsdA-CTA$_2$/B was binding and transporting into Vero and DC2.4 cells. Cells were incubated with IsdA-CTA$_2$/B for 45 minutes at 4° C. to inhibit, or at 37° C. to promote cellular uptake.

EXAMPLE 3

The chimeric proteins were tested for their specific humoral response.

BALB/c mice were mock immunized or immunized intranasally with IsdA-CTA$_2$/B, IsdA plus CTA$_2$/B mixed, or IsdA on day 0 and boosted on day 10 (Table 1 below). FIG. 6 shows systemic antibody response to IsdA-CTA$_2$/B in vivo. Referring to FIG. 6, sera collected on days 0, 10, 14, and 45 were pooled by treatment group at each time point and tested for recognition of IsdA by IgG ELISA. IsdA-specific serum IgG endpoint titers from mice immunized with IsdA-CTA$_2$/B were significantly higher than those of mock-immunized mice on day 10, than those of all control groups on day 14, and than those of mice immunized with IsdA alone and mock-immunized mice on day 45. As used herein, "*" denotes statistical significance (P<0.05) between mice immunized with IsdA-CTA$_2$/B versus controls. Nasal, intestinal, and vaginal washes were collected on day 45, pooled by treatment group, and tested for recognition of IsdA by IgA ELISA.

Figure 7:
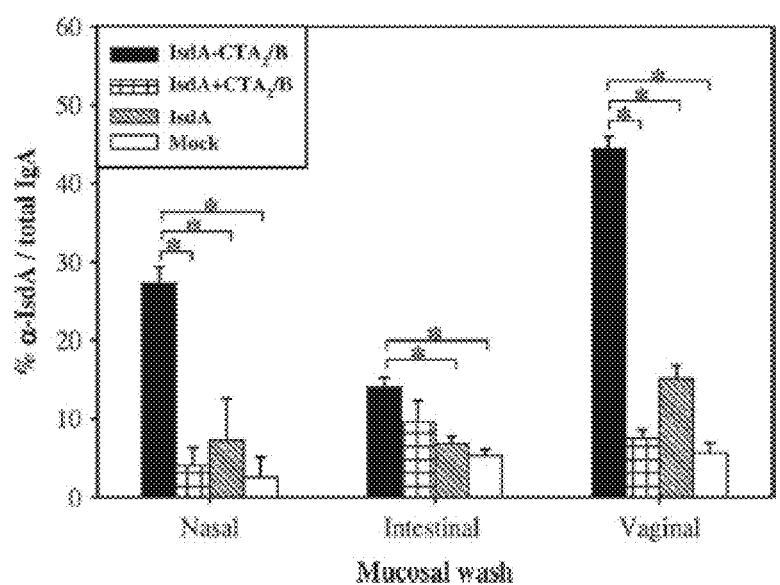
FIG. 7 shows a plot illustrating in vivo mucosal antibody response to chimeric protein according to some embodiments.

FIG. 7 shows mucosal antibody response to IsdA-CTA$_2$/B in vivo. Referring to FIG. 7, the percentage of IsdA-IgA out of total IgA was significantly higher in nasal and vaginal washes from mice immunized with IsdA-CTA$_2$/B than from mock-immunized mice, mice immunized with IsdA plus CTA$_2$/B, or mice immunized with IsdA alone. In addition, intestinal IsdA-IgA was significantly higher in IsdA-CTA$_2$/B-immunized mice than in IsdA- and mock-immunized mice (FIG. 7). Together, these results suggest that IsdA specific systemic and mucosal humoral immunity can be stimulated after intranasal vaccination with the IsdA-CTA$_2$/B chimera.

TABLE 1

Immunization Strategy.

| Antigen/ adjuvant | Dose per vaccination (□ g) | $n^b$ | Days of intranasal vaccination | Days of sampling | |
|---|---|---|---|---|---|
| | | | | Sera | Mucosal secretions and spleen (n) |
| IsdA-CTA$_2$/B chimera | 50 | 8 | 0, 10 | 0, 10, 14, 45 | 14 (2), 45 (6) |
| IsdA + CTA$_2$/B | 17 + 33$^a$ | 8 | 0, 10 | 0, 10, 14, 45 | 14 (2), 45 (6) |
| IsdA | 17 | 8 | 0, 10 | 0, 10, 14, 45 | 14 (2), 45 (6) |
| Mock | NA$^c$ | 8 | 0, 10 | 0, 10, 14, 45 | 14 (2), 45 (6) |

$^a$Concentrations are according to equimolar to equimolar amounts of IsdA
$^b$n, number of mice
$^c$NA, not applicable

EXAMPLE 4

Figure 9:
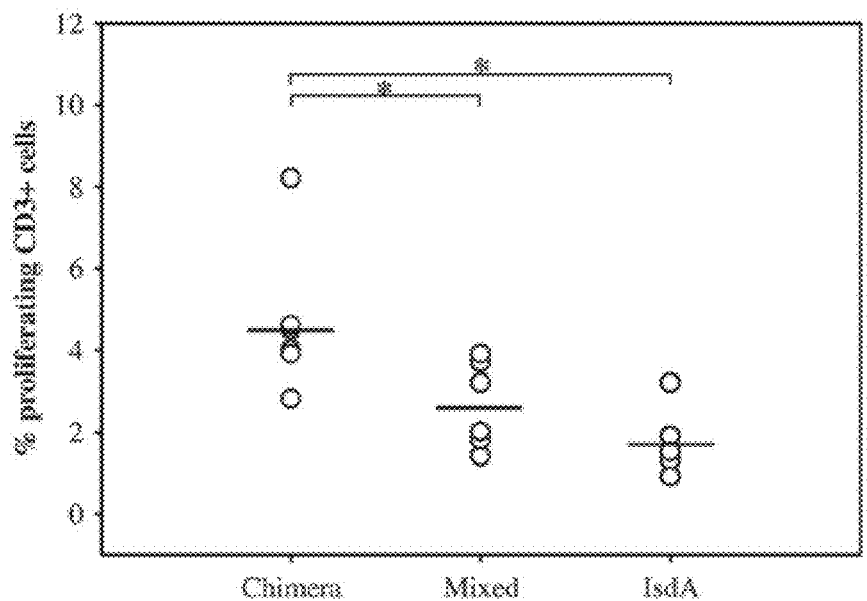
FIG. 9 shows a plot summarizing the flow cytometry results shown in FIGS. 8A-8D according to some embodiments.

Cellular proliferation of IsdA-stimulated splenocytes was assessed using flow cytometry and a resazurin-based fluorescent dye assay. CFSE-based flow cytometric results suggest that day 45 splenocytes derived from mice immunized with IsdA-CTA$_2$/B showed significant proliferation of IsdA-specific CD3+ T lymphocytes compared with mixed and IsdA control groups (FIGS. 8A-8D and 9). Referring to FIGS. 8A-8D, CFSE-labeled splenocytes were cultured in vitro for 84 h with IsdA and stained with anti-CD3-PE-Cy5. Referring to FIG. 9, percent proliferation of IsdA-specific CD3+ T lymphocytes from individual mice on day 45 was determined by flow cytometry. Mock samples contained low numbers of CD3+ T lymphocytes.

Figure 10:
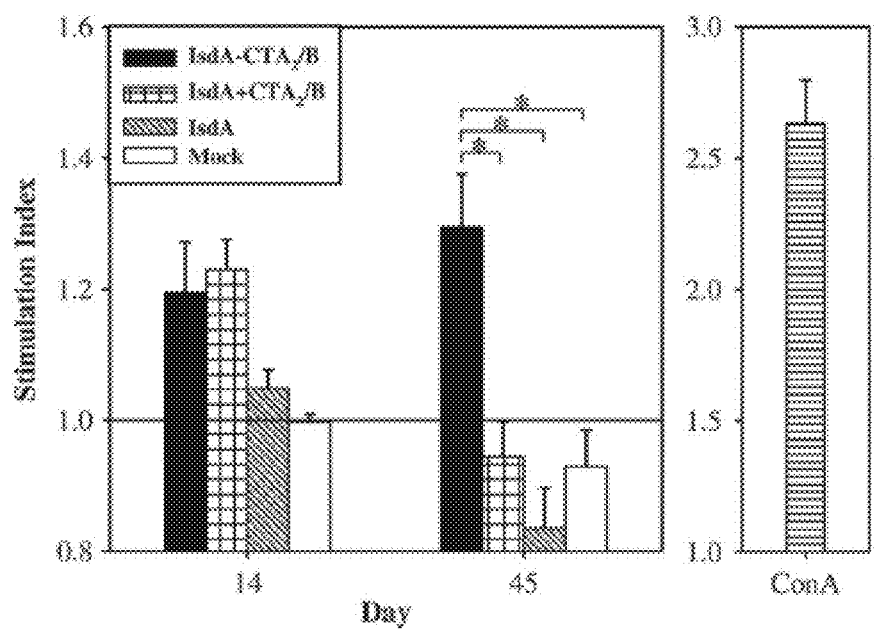
FIG. 10 shows a plot showing the results of Resazurin assay of splenocytes from mice immunized with chimeric protein according to some embodiments.

FIG. 10 shows the result of a resazurin assay of splenocytes from days 14 and 45 cultured in vitro for 84 h with IsdA. The resazurin assays revealed that in vitro stimulation of splenocytes from IsdA-CTA$_2$/B-immunized mice induced significant proliferation compared with IsdA plus CTA$_2$/B, IsdA, and mock groups on day 45 (FIG. 10). With the low sample size (n=2 per group) on day 14, no significance was observed between groups. Error bars are based on n=2 (day 14) or n=6 (day 45). Stimulation was observed for the positive control, ConA. These results suggest that intranasal administration of IsdA-CTA$_2$/B can induce a cellular activation response.

EXAMPLE 5

Figure 11:
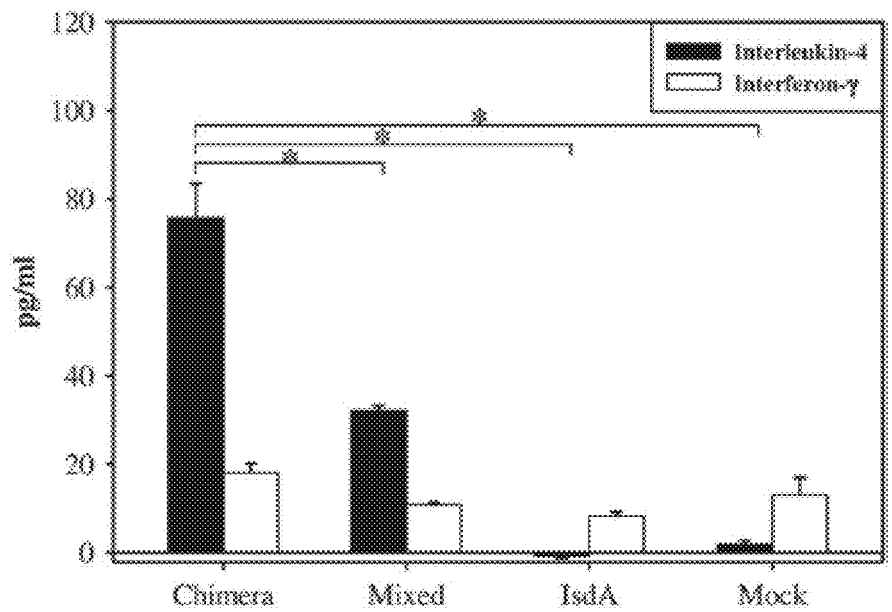
FIG. 11 shows a plot showing IL-4 and IN-□ levels of antigen-stimulated splenocytes from mice immunized with chimeric protein according to some embodiments.

The levels of IL-4 and IFN-□□ in supernatants of splenocytes stimulated with IsdA in vitro were determined by ELISA. Referring to FIG. 11, IL-4 and IFN-□□ levels in culture supernatants from splenocytes, pooled by immunization group (n=6), were stimulated in vitro for 84 h with IsdA and measured by ELISA. The splenocytes obtained from mice immunized with IsdA-CTA$_2$/B secreted high levels of IL-4, and these levels were significantly higher than levels of all controls (FIG. 11). Although the level of IFN-☐☐ was slightly higher in IsdA-CTA$_2$/B-immune splenocytes, low levels of IFN-☐☐, near the detection limit for the assay, were found in all groups (FIG. 11).

Figure 12:
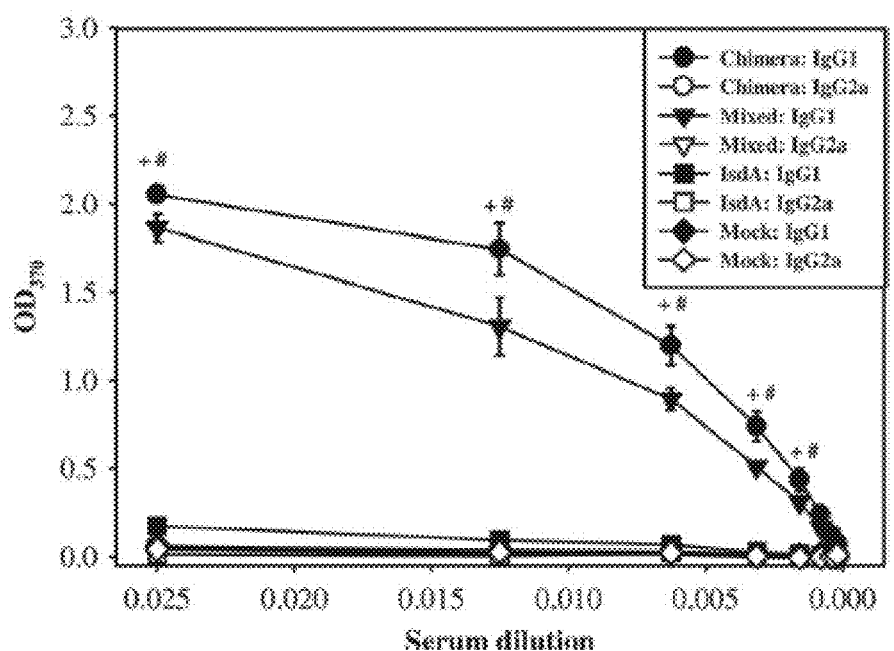
FIG. 12 shows a plot showing the results of IsdA-specific ELISA titrations of systemic antibody subtypes according to some embodiments.

FIG. 12 shows IsdA-specific IgG1 and IgG2a ELISA titrations from day 45 sera pooled by immunization group (n=6). Titrations of IgG1 and IgG2a revealed that immunization with IsdA-CTA$_2$/B drove isotype switching primarily to the IgG1 subclass although minute IgG2a levels were also detected. These results suggest that immunization with IsdA-CTA$_2$/B promotes a Th2-type immune response.

EXAMPLE 6

Figure 13A:
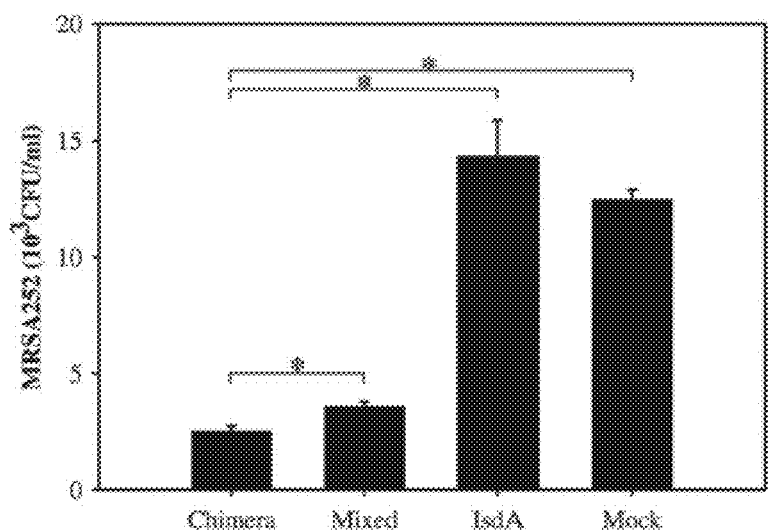
FIGS. 13A-13B show a plot showing the effects of immune serum on *S. aureus* adhesion to human epithelial cells according to some embodiments.
Figure 13B:
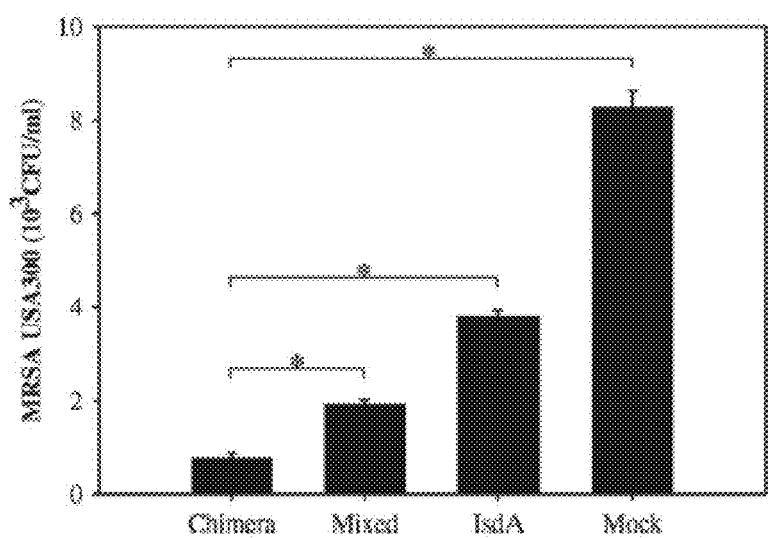

Pooled sera from commonly immunized mice were used to investigate the ability of immune serum to functionally block adherence of *S. aureus* to human epithelial cells (HeLa). FIGS. 13A-13B shows the effect of immune serum on *S. aureus* adhesion to human epithelial cells in vitro. Referring to FIG. 13A, sera (1:100; day 45) was pooled by immunization group and incubated with MRSA252 (5×10$^7$ CFU) for 1 h at 37° C. and then added to confluent HeLa cells. After washing and lysis, the number of internalized and cell-bound bacteria was enumerated. Preincubation of the *S. aureus* strain used for vaccination (MRSA252) with day 45 sera from IsdA-CTA$_2$/B-immunized mice significantly reduced bacterial adhesion to epithelial cells compared to all control groups (FIG. 13A).

FIG. 13B shows the result of similar tests performed with MRSA USA300 (5×10$^9$ CFU). Referring to FIG. 13B, there was a significant reduction in bacterial adhesion to human epithelial cells after a different strain of *S. aureus* (MRSA USA300) was preincubated with day 45 sera from mice immunized with IsdA-CTA$_2$/B (FIG. 13B).

These examples suggest that the chimeric proteins of the present invention can bind and transport into epithelial and dendritic cells as consistent with the uptake of CT involving retrograde movement to the perinuclear domain of the Golgi apparatus and endoplasmic reticulum. It is believed that the ability of the chimeric proteins to bind to GM1 and trigger internalization leads to the activation of immune effector cells by the CTB subunit and promotes antigen presentation on MHC molecules.

Moreover, the ELISAs of IsdA-specific responses from the sera and nasal, intestinal, and vaginal fluids of intranasally immunized mice verifies that the chimeric proteins can induce antigen-specific systemic and mucosal immunity in mice. As expected, IgG titers were highest on day 14 after the boost and began to diminish by day 45.

These results also suggest the characteristic ability of CT to induce systemic IgG to antigens co-administered with CT at mucosal sites. The presence of IsdA-specific IgA in nasal, intestinal, and vaginal fluids after intranasal immunization with IsdA-CTA$_2$/B suggests that IgA blasts migrated from the nasal-associated lymphoid tissue into distal mucosal effector sites in the nasal passage and gastrointestinal and genital tracts. Thus, it is believed that CT and CT derivatives promote more of a Th2-type response, which is typically characterized by secretion of IL-4 leading to induction of antibody class switching to non-complement-activating IgG1. In vitro functional assays of antibodies revealed a significant reduction in internalized and cell-bound bacteria on human epithelial cells after preincubation of IsdA-CTA$_2$/B immune serum with the *S. aureus* isolate used for vaccination, MRSA252. Additionally, antibodies were able to prevent adhesion of MRSA USA300.

IsdA from MRSA252 and MRSA USA300 has 92% amino acid identity with the majority of differences present within the C terminus, which suggests that antibodies against IsdA are functional in vitro and may protect against multiple serotypes in vivo.

The results also suggest that the humoral and cellular responses induced by IsdA-CTA$_2$/B are superior to those stimulated by a mixed preparation of antigen and adjuvant (IsdA plus CTA$_2$/B). Thus, the structure of the IsdA-CTA$_2$/B chimera is optimal for the induction of antigen-specific humoral responses and potentially for presentation on MHC molecules.

EXAMPLE 7

Milk anti-IsdA IgA titer levels were measured in cows treated with a chimeric protein according to one or more embodiments of the present invention. Six (1-6 in FIG. 14) clinically healthy Holstein dairy cows were vaccinated intranasally on day 0 with 300 ☐g of IsdA-CTA2/B chimera (cows 4-6) or an equivalent concentration of IsdA alone (cows 1-3). Cows were boosted on day 14 with the same concentration. Milk was collected on days 0, 14 and 28 and analyzed by IsdA-specific IgA ELISA.

Figure 14:
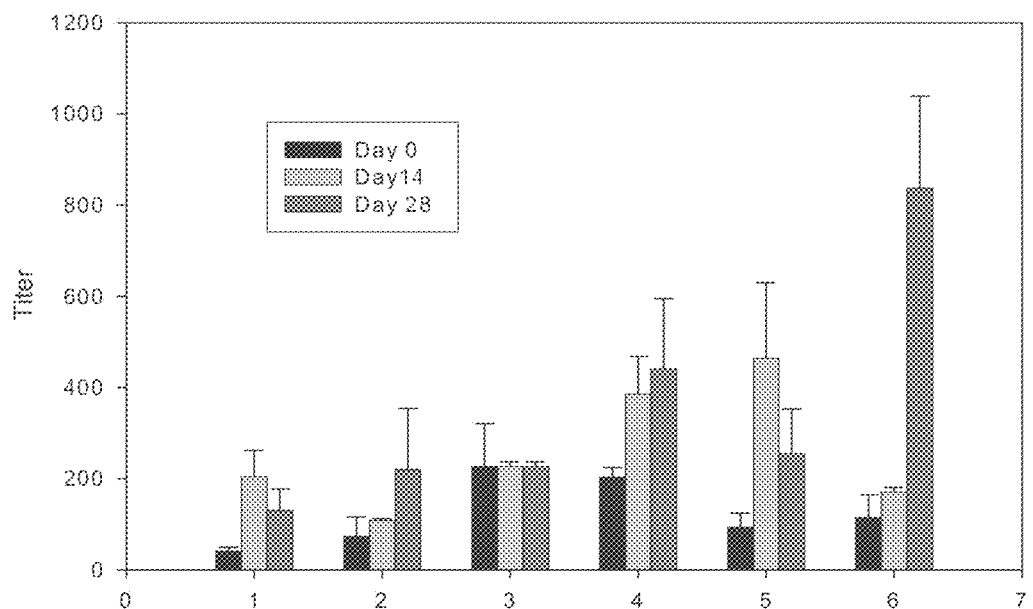
FIG. 14 shows a plot showing milk anti-IsdA IgA titers in cows.

FIG. 14 shows a summary of the titer results. The titer values were calculated as the reciprocal of the milk dilution that was 0.1 O.D. above background. Referring to FIG. 14, cows 1 (2296), 2 (2299) and 3 (2403) represent controls of the experiment while cows 4 (2319), 5 (2340) and 6 (2472) were vaccinated (labeled *) with a chimeric protein. Cows 4-6 all displayed increases in the titer on days 14 and 28 as compared to cows 1-3.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A chimeric protein comprising an amino acid sequence that is at least 90% identical to SEQ ID NO: 2 or an amino acid sequence that is at least 90% identical to SEQ ID NO: 3 and a truncated iron-regulated surface determinant A (IsdA) protein of *S. aureus* of SEQ ID NO: 4 as present within the amino acid sequence of SEQ ID NO: 5 or SEQ ID NO: 6.

2. The chimeric protein of claim 1 and an adjuvant protein selected from the group consisting of cholera toxin, heat-labile toxin and shiga toxin.

3. The chimeric protein of claim 2, wherein said adjuvant protein is selected from the group consisting of cholera toxin subunit A (CTA), cholera toxin subunit B (CTB), heat-labile toxin subunit B and shiga toxin subunit B.

4. The chimeric protein of claim 3, wherein said CTA adjuvant is $CTA_2$ or said CTB adjuvant is CTB.

5. The chimeric protein of claim 4, wherein said $CTA_2$ has the amino acid sequence of SEQ ID NO: 2.

6. The chimeric protein of claim 4, wherein said CTB has the amino acid sequence of SEQ ID NO: 3.

7. The chimeric protein of claim 5, wherein the chimeric protein has the amino acid sequence of SEQ ID NO: 6.

8. The chimeric protein of claim 6, wherein the chimeric protein has the amino acid sequence of SEQ ID NO: 5.

9. The chimeric protein of claim 2, wherein the chimeric protein is a fusion protein.

10. An immunogenic composition comprising the chimeric protein of claim 1.

11. An immunogenic composition comprising the chimeric protein of claim 7.

12. An immunogenic composition comprising the chimeric protein of claim 8.

* * * * *

SEQUENCE LISTING

<160> NUMBER OF SEQ ID NOS: 21

<210> SEQ ID NO 1
<211> LENGTH: 193
<212> TYPE: PRT
<213> ORGANISM: Vibrio cholerae

<400> SEQUENCE: 1

Asn Asp Asp Lys Leu Tyr Arg Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile
    50                  55                  60

Ser Leu Arg Ser Ala His Leu Val Gly Gln Thr Ile Leu Ser Gly His
65                  70                  75                  80

Ser Thr Tyr Tyr Ile Tyr Val Ile Ala Thr Ala Pro Asn Met Phe Asn
                85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Cys Gly Asn Ala Pro Arg
            180                 185                 190

Ser

<210> SEQ ID NO 2
<211> LENGTH: 47
<212> TYPE: PRT
<213> ORGANISM: Vibrio cholerae

<400> SEQUENCE: 2

Ser Met Ser Asn Thr Ser Asp Glu Lys Thr Gln Ser Leu Gly Val Lys
1               5                   10                  15

Phe Leu Asp Glu Tyr Gln Ser Lys Val Lys Arg Gln Ile Phe Ser Gly
            20                  25                  30

Tyr Gln Ser Asp Ile Asp Thr His Asn Arg Ile Lys Asp Glu Leu
        35                  40                  45

<210> SEQ ID NO 3
<211> LENGTH: 103
<212> TYPE: PRT
<213> ORGANISM: Vibrio cholerae

<400> SEQUENCE: 3

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

```
Gly Lys Arg Glu Met Ala Ile Ile Thr Phe Lys Asn Gly Ala Thr Phe
             35                  40                  45

Gln Val Glu Val Pro Gly Ser Gln His Ile Asp Ser Gln Lys Lys Ala
 50                  55                  60

Ile Glu Arg Met Lys Asp Thr Leu Arg Ile Ala Tyr Leu Thr Glu Ala
 65                  70                  75                  80

Lys Val Glu Lys Leu Cys Val Trp Asn Asn Lys Thr Pro His Ala Ile
                 85                  90                  95

Ala Ala Ile Ser Met Ala Asn
                100
```

```
<210> SEQ ID NO 4
<211> LENGTH: 273
<212> TYPE: PRT
<213> ORGANISM: Staphylococcus aureus

<400> SEQUENCE: 4
```

```
Ala Thr Glu Ala Thr Asn Ala Thr Asn Gln Ser Thr Gln Val Ser
 1               5                  10                  15

Gln Ala Thr Ser Gln Pro Ile Asn Phe Gln Val Gln Lys Asp Gly Ser
                 20                  25                  30

Ser Glu Lys Ser His Met Asp Asp Tyr Met Gln His Pro Gly Lys Val
             35                  40                  45

Ile Lys Gln Asn Asn Lys Tyr Tyr Phe Gln Ala Val Leu Asn Asn Ala
 50                  55                  60

Ser Phe Trp Lys Glu Tyr Lys Phe Tyr Asn Ala Asn Asn Gln Glu Leu
 65                  70                  75                  80

Ala Thr Thr Val Val Asn Asp Asp Lys Lys Ala Asp Thr Arg Thr Ile
                 85                  90                  95

Asn Val Ala Val Glu Pro Gly Tyr Lys Ser Leu Thr Thr Lys Val His
                100                 105                 110

Ile Val Val Pro Gln Ile Asn Tyr Asn His Arg Tyr Thr Thr His Leu
                115                 120                 125

Glu Phe Glu Lys Ala Ile Pro Thr Leu Ala Asp Ala Ala Lys Pro Asn
130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Lys Val Lys Pro Ala
                165                 170                 175

Val Thr Ala Pro Ser Lys Asn Glu Asn Arg Gln Thr Thr Lys Val Val
                180                 185                 190

Ser Ser Glu Ala Thr Lys Asp Gln Ser Gln Thr Gln Ser Ala Arg Thr
            195                 200                 205

Val Lys Thr Thr Gln Thr Ala Gln Asp Gln Asn Lys Val Gln Thr Pro
210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Asp Ser Lys Ala Lys Glu Leu Pro
                260                 265                 270

Lys
```

```
<210> SEQ ID NO 5
<211> LENGTH: 423
```

<212> TYPE: PRT
<213> ORGANISM: Artificial Sequence
<220> FEATURE:
<223> OTHER INFORMATION: Chimeric Protein IsdA-CTA2/B

<400> SEQUENCE: 5

```
Ala Thr Glu Ala Thr Asn Ala Thr Asn Asn Gln Ser Thr Gln Val Ser
1               5

```
Ile Glu Arg Met Lys Asp Thr Leu Arg Ile Ala Tyr Leu Thr Glu Ala
385                 390                 395                 400

Lys Val Glu Lys Leu Cys Val Trp Asn Asn Lys Thr Pro His Ala Ile
                405                 410                 415

Ala Ala Ile Ser Met Ala Asn
            420

<210> SEQ ID NO 6
<211> LENGTH: 320
<212> TYPE: PRT
<213> ORGANISM: Artificial Sequence
<220> FEATURE:
<223> OTHER INFORMATION: Chimeric Protein Isda-CTA2

<400> SEQUENCE: 6

Ala Thr Glu Ala Thr Asn Ala Thr Asn Asn Gln Ser Thr Gln Val Ser
1               5                   10                  15

Gln

<210> SEQ ID NO 7
<211> LENGTH: 193
<212> TYPE: PRT
<213> ORGANISM: Escherichia coli

<400> SEQUENCE: 7

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Ser Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr

<210> SEQ ID NO 8
<211> LENGTH: 47
<212> TYPE: PRT
<213> ORGANISM: Escherichia coli

<400> SEQUENCE: 8

Ile Thr Gly Asp Thr Cys Asn Glu Glu Thr Gln Asn Leu Ser Thr Ile
1               5                   10                  15

Tyr Leu Arg Lys Tyr Gln Ser Lys Val Lys Arg Gln Ile Phe Ser Asp
            20                  25                  30

Tyr Gln Ser Glu Val Asp Ile Tyr Asn Arg Ile Arg Asn Glu Leu
        35                  40                  45

<210> SEQ ID NO 9
<211> LENGTH: 103
<212> TYPE: PRT
<213> ORGANISM: Escherichia coli

<400> SEQUENCE: 9

Ala Pro Gln Ser Ile Thr Glu Leu Cys Ser Tyr His Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

```
Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100
```

<210> SEQ ID NO 10
<211> LENGTH: 423
<212> TYPE: PRT
<213> ORGANISM: Artificial Sequence
<220> FEATURE:
<223> OTHER INFORMATION: Chimeric Protein IsdA-LTA2/B

<400> SEQUENCE: 10

```
Ala Thr Glu Ala Thr Asn Ala Thr Asn Gln Ser Thr Gln Val Ser
1               5                   10                  15

Gln Ala Thr Ser Gln Pro Ile Asn Phe Gln Val Gln Lys Asp Gly Ser
                20                  25                  30

Ser Glu Lys Ser His Met Asp Asp Tyr Met Gln His Pro Gly Lys Val
            35                  40                  45

Ile Lys Gln Asn Asn Lys Tyr Tyr Phe Gln Ala Val Leu Asn Asn Ala
        50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Lys Val Lys Pro Ala
                165                 170                 175

Val Thr Ala Pro Ser Lys Asn Glu Asn Arg Gln Thr Thr Lys Val Val
                180                 185                 190

Ser Ser Glu Ala Thr Lys Asp Gln Ser Gln Thr Gln Ser Ala Arg Thr
            195                 200                 205

Val Lys Thr Thr Gln Thr Ala Gln Asp Gln Asn Lys Val Gln Thr Pro
        210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Asp Ser Lys Ala Lys Glu Leu Pro
                260                 265                 270

Lys Ile Thr Gly Asp Thr Cys Asn Glu Glu Thr Gln Asn Leu Ser Thr
            275                 280                 285

Ile Tyr Leu Arg Lys Tyr Gln Ser Lys Val Lys Arg Gln Ile Phe Ser
        290                 295                 300
```

```
Asp Tyr Gln Ser Glu Val Asp Ile Tyr Asn Arg Ile Arg Asn Glu Leu
305                 310                 315                 320

Ala Pro Gln Ser Ile Thr Glu Leu Cys Ser Glu Tyr His Asn Thr Gln
            325                 330                 335

Ile Tyr Thr Ile Asn Asp Lys Ile Leu Ser Tyr Thr Glu Ser Met Ala
        340                 345                 350

Gly Lys Arg Glu Met Val Ile Ile Thr Phe Lys Ser Gly Ala Thr Phe
    355                 360                 365

Gln Val Glu Val Pro Gly Ser Gln His Ile Asp Ser Gln Lys Lys Ala
370                 375                 380

Ile Glu Arg Met Lys Asp Thr Leu Arg Ile Thr Tyr Leu Thr Glu Thr
385                 390                 395                 400

Lys Ile Asp Lys Leu Cys Val Trp Asn Asn Lys Thr Pro Asn Ser Ile
            405                 410                 415

Ala Ala Ile Ser Met Glu Asn
            420

<210> SEQ ID NO 11
<211> LENGTH: 320
<212> TYPE: PRT
<213> ORGANISM: Artificial Sequence
<220> FEATURE:
<223> OTHER INFORMATION: Chimeric Protein IsdA-LTA2

<400> SEQUENCE: 11

Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Lys Lys Ala Asp Thr Arg Thr Ile
            85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
            165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Lys Ser Glu Ser Asn Asn Gln Ala Val
225                 230                 235                 240
```

```
Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270

Lys Ile Thr Gly Asp Thr Cys Asn Glu Glu Thr Gln Asn Leu Ser Thr
            275                 280                 285

Ile Tyr Leu Arg Lys Tyr Gln Ser Lys Val Lys Arg Gln Ile Phe Ser
        290                 295                 300

Asp Tyr Gln Ser Glu Val Asp Ile Tyr Asn Arg Ile Arg Asn Glu Leu
305                 310                 315                 320

<210> SEQ ID NO 12
<211> LENGTH: 250
<212> TYPE: PRT
<213> ORGANISM: Escherichia coli

<400> SEQUENCE: 12

Glu Phe Thr Leu Asp Phe Ser Thr Ala Lys Thr Tyr Val Asp Ser Leu
1               5                   10                  15

Asn Val Ile Arg Ser Ala Ile Gly Thr Pro Leu Gln Thr Ile Ser Ser
            20                  25                  30

Gly Gly Thr Ser Leu Leu Met Ile Asp Ser Gly Thr Gly Asp Asn Leu
        35                  40                  45

Phe Ala Val Asp Val Arg Gly Ile Asp Pro Glu Glu Gly Arg Phe Asn
    50                  55                  60

Asn Leu Arg Leu Ile Val Glu Arg Asn Asn Leu Tyr Val Thr Gly Phe
65                  70                  75                  80

Val Asn Arg Thr Asn Asn Val Phe Tyr Arg Phe Ala Asp Phe Ser His
                85                  90                  95

Val Thr Phe Pro Gly Thr Thr Ala Val Thr Leu Ser Gly Asp Ser Ser
            100                 105                 110

Tyr Thr Thr Leu Gln Arg Val Ala Gly Ile Ser Arg Thr Gly Met Gln
        115                 120                 125

Ile Asn Arg His Ser Leu Thr Thr Ser Tyr Leu Asp Leu Met Ser His
    130                 135                 140

Ser Gly Thr Ser Leu Thr Gln Ser Val Ala Arg Ala Met Leu Arg Phe
145                 150                 155                 160

Val Thr Val Thr Ala Glu Ala Leu Arg Phe Arg Gln Ile Gln Arg Gly
                165                 170                 175

Phe Arg Thr Thr Leu Asp Asp Leu Ser Gly Arg Ser Tyr Val Met Thr
            180                 185                 190

Ala Glu Asp Val Asp Leu Thr Leu Asn Trp Gly Arg Leu Ser Ser Val
        195                 200                 205

Leu Pro Asp Tyr His Gly Gln Asp Ser Val Arg Val Gly Arg Ile Ser
    210                 215                 220

Phe Gly Ser Ile Asn Ala Ile Leu Gly Ser Val Ala Leu Ile Leu Asn
225                 230                 235                 240

Cys His His His Ala Ser Arg Val Ala Arg
                245                 250

<210> SEQ ID NO 13
<211> LENGTH: 42
<212> TYPE: PRT
<213> ORGANISM: Escherichia coli

<400> SEQUENCE: 13
```

```
Met Ala Ser Asp Glu Phe Pro Ser Met Cys Pro Ala Asp Gly Arg Val
1               5                   10                  15

Arg Gly Ile Thr His Asn Lys Ile Leu Trp Asp Ser Thr Leu Gly
            20                  25                  30

Ala Ile Leu Met Arg Arg Thr Ile Ser Ser
            35                  40
```

<210> SEQ ID NO 14
<211> LENGTH: 69
<212> TYPE: PRT
<213> ORGANISM: Escherichia coli

<400> SEQUENCE: 14

```
Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Ser Ala Gln Ile Thr Gly Met
            35                  40                  45

Thr Val Thr Ile Lys Thr Asn Ala Cys His Asn Gly Gly Phe Ser
    50                  55                  60

Glu Val Ile Phe Arg
65
```

<210> SEQ ID NO 15
<211> LENGTH: 384
<212> TYPE: PRT
<213> ORGANISM: Artificial Sequence
<220> FEATURE:
<223> OTHER INFORMATION: Chimeric Protein IsdA-STA2/B

<400> SEQUENCE: 15

```
Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
            35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
            115                 120                 125

Glu Phe Glu Lys Ala Ile Pro Thr Leu Ala Asp Ala Lys Pro Asn
            130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190
```

```
Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
                260                 265                 270

Lys Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser Thr Pro Asp Cys Val
305                 310                 315                 320

Thr Gly Lys Val Glu Tyr Thr Lys Tyr Asn Asp Asp Thr Phe Thr
                325                 330                 335

Val Lys Val Gly Asp Lys Glu Leu Phe Thr Asn Arg Trp Asn Leu Gln
                340                 345                 350

Ser Leu Leu Leu Ser Ala Gln Ile Thr Gly Met Thr Val Thr Ile Lys
                355                 360                 365

Thr Asn Ala Cys His Asn Gly Gly Phe Ser Glu Val Ile Phe Arg
        370                 375                 380

<210> SEQ ID NO 16
<211> LENGTH: 315
<212> TYPE: PRT
<213> ORGANISM: Artificial Sequence
<220> FEATURE:
<223> OTHER INFORMATION: Chimeric Protein IsdA-STA2

<400> SEQUENCE: 16

Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175
```

-continued

```
Val Thr Ala Pro Ser Lys Asn Glu Asn Arg Gln Thr Lys Val Val
            180                 185                 190
Ser Ser Glu Ala Thr Lys Asp Gln Ser Gln Thr Gln Ser Ala Arg Thr
        195                 200                 205
Val Lys Thr Thr Gln Thr Ala Gln Asp Gln Asn Lys Val Gln Thr Pro
    210                 215                 220
Val Lys Asp Val Ala Thr Ala Lys Ser Glu Ser Asn Asn Gln Ala Val
225                 230                 235                 240
Ser Asp Asn Lys Ser Gln Gln Thr Asn Lys Val Thr Lys Gln Asn Glu
                245                 250                 255
Val His Lys Gln Gly Pro Ser Leu Asp Ser Lys Ala Lys Glu Leu Pro
            260                 265                 270
Lys Met Ala Ser Asp Glu Phe Pro Ser Met Cys Pro Ala Asp Gly Arg
        275                 280                 285
Val Arg Gly Ile Thr His Asn Lys Ile Leu Trp Asp Ser Ser Thr Leu
    290                 295                 300
Gly Ala Ile Leu Met Arg Arg Thr Ile Ser Ser
305                 310                 315
```

<210> SEQ ID NO 17
<211> LENGTH: 32
<212> TYPE: DNA
<213> ORGANISM: Artificial Sequence
<220> FEATURE:
<223> OTHER INFORMATION: 5' SphI PCR primer

<400> SEQUENCE: 17
gctactggca tgcggcaaca gaagctacga ac                                32

<210> SEQ ID NO 18
<211> LENGTH: 30
<212> TYPE: DNA
<213> ORGANISM: Artificial Sequence
<220> FEATURE:
<223> OTHER INFORMATION: 3' ClaI Primer

<400> SEQUENCE: 18
gtgcatgatc gattttggta attctttagc                                   30

<210> SEQ ID NO 19
<211> LENGTH: 33
<212> TYPE: DNA
<213> ORGANISM: Artificial Sequence
<220> FEATURE:
<223> OTHER INFORMATION: 5' BamHI Primer

<400> SEQUENCE: 19
gctactggat ccgcggcaac agaagctacg aac                               33

<210> SEQ ID NO 20
<211> LENGTH: 36
<212> TYPE: DNA
<213> ORGANISM: Artificial Sequence
<220> FEATURE:
<223> OTHER INFORMATION: 5' BamHI alternative primer

<400> SEQUENCE: 20
gtgcataagc tttcaagttt ttggtaattc tttagc                            36

<210> SEQ ID NO 21
<211> LENGTH: 30
<212> TYPE: DNA

-continued

```
<213> ORGANISM: Artificial Sequence
<220> FEATURE:
<223> OTHER INFORMATION: 3' HindIII Primer

<400> SEQUENCE: 21
gtgcatgatc gattttggta attctttagc                                     30
```